United States Patent
Russinger

(10) Patent No.: US 7,076,018 B2
(45) Date of Patent: Jul. 11, 2006

(54) TOMOGRAPHY APPARATUS WITH GANTRY-CARRIED COMPONENT MOUNTED TO WITHSTAND CENTRIFUGAL FORCES

(75) Inventor: Johann Russinger, Buckenhof (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/187,249

(22) Filed: Jul. 22, 2005

(65) Prior Publication Data

US 2006/0018437 A1   Jan. 26, 2006

(30) Foreign Application Priority Data

Jul. 23, 2004   (DE) .................. 10 2004 035 790

(51) Int. Cl.
*H05G 1/60*   (2006.01)
*H05G 1/02*   (2006.01)

(52) U.S. Cl. .................. 378/15; 378/193; 378/197

(58) Field of Classification Search ............... 378/4, 378/15, 193, 196, 197; 250/363.08, 363.05
See application file for complete search history.

(56) References Cited

U.S. PATENT DOCUMENTS

| 5,703,921 A * | 12/1997 | Fujita et al. ............. 378/4 |
| 6,314,157 B1 * | 11/2001 | Tachizaki .................. 378/4 |
| 6,404,845 B1 * | 6/2002 | Sharpless et al. ......... 378/15 |
| 6,452,998 B1 * | 9/2002 | Tybinkowski et al. ..... 378/17 |

\* cited by examiner

*Primary Examiner*—Edward J. Glick
*Assistant Examiner*—Irakli Kiknadze
(74) *Attorney, Agent, or Firm*—Schiff Hardin LLP

(57) ABSTRACT

The gantry of a tomography apparatus has a drum that is rotatable around an axis. The drum carries at least one component mounted thereon. The component is mounted on the drum by a mounting arrangement that resolves a centrifugal force acting on the component into a radial force vector and a substantially axially proceeding force vector. The mounting of the component is thereby made less susceptible to breakage due to the high centrifugal forces that occur upon rotation of the gantry.

10 Claims, 3 Drawing Sheets

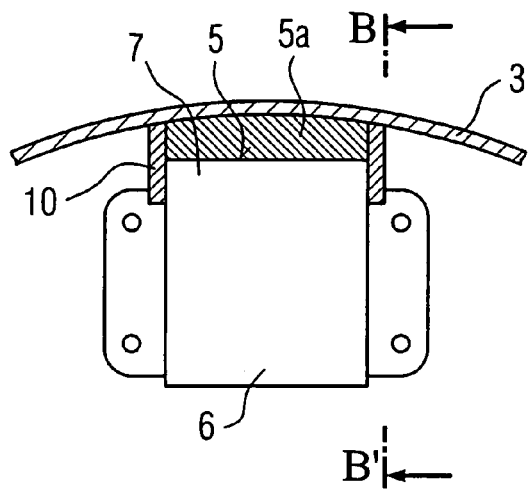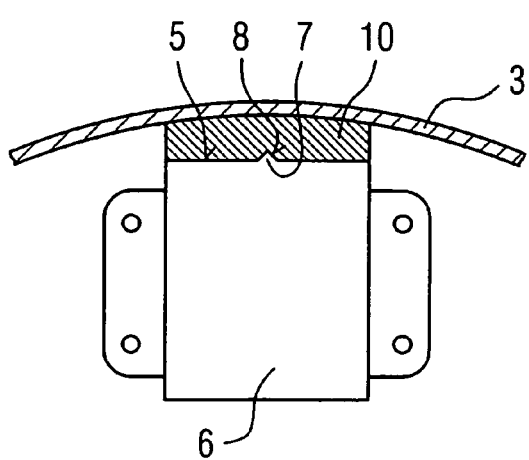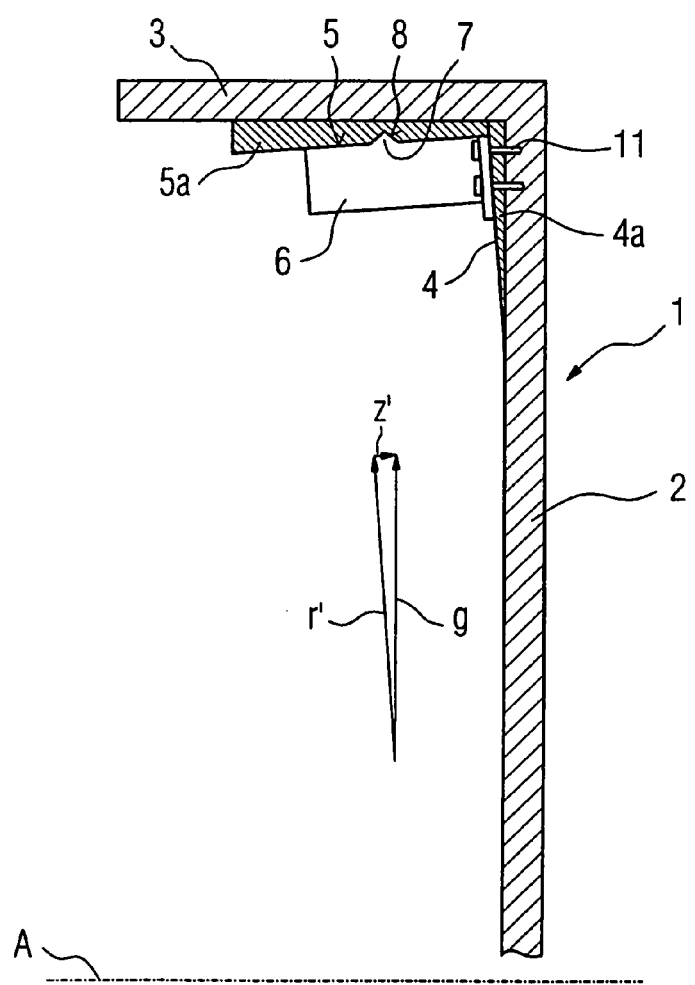

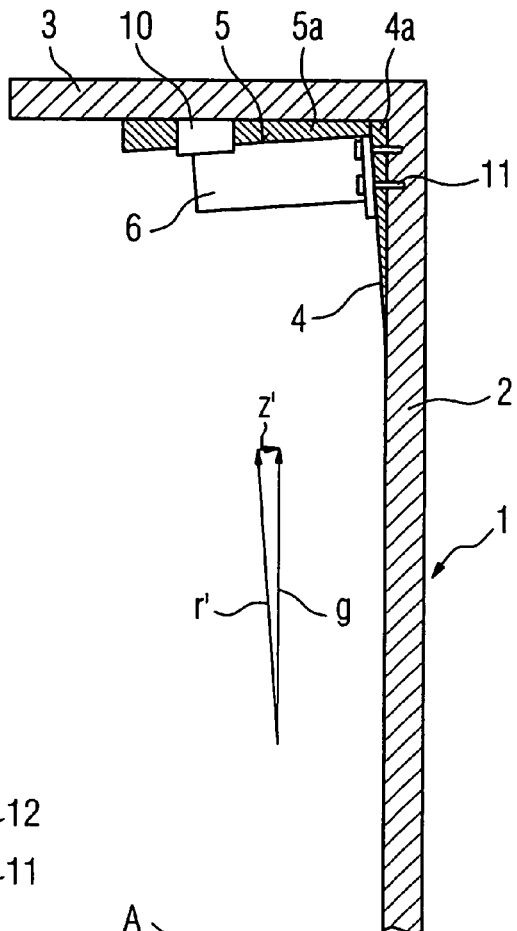
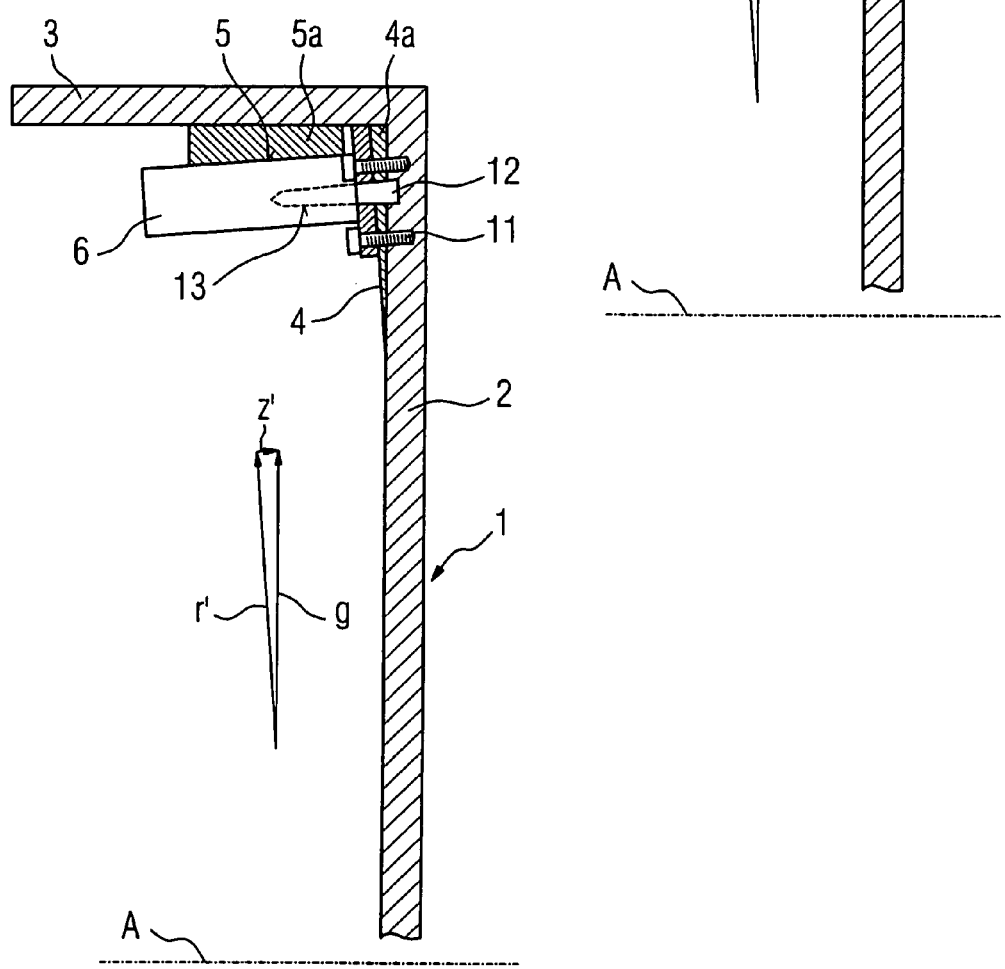

TOMOGRAPHY APPARATUS WITH GANTRY-CARRIED COMPONENT MOUNTED TO WITHSTAND CENTRIFUGAL FORCES

BACKGROUND OF THE INVENTION

1. Field of the Invention

The present invention concerns a tomography apparatus, in particular an x-ray computed tomography apparatus.

2. Description of the Prior Art

A conventional x-ray computed tomography apparatus comprises a gantry with a drum that can be rotated around a patient bed, which carries, among other things, x-ray source and a detector disposed opposite each other. In x-ray computed tomography systems of newer design, the drum is rotated with a considerable speed of up to 180 revolutions/minute. Centrifugal forces equal 20 to 30 times the acceleration due to gravity thereby act on the components housed in or carried by the drum. As a result, fastening elements with which the components are mounted to the drum subjected to a particularly high stress. Fastening elements may break and causing a component to detach from the drum. This can lead to damage to the x-ray computed tomography or to endangerment of personnel in its vicinity.

SUMMARY OF THE INVENTION

An object of the present invention is to avoid the disadvantages in a tomography apparatus wherein the components attached to the drum are always securely and reliably retained given exposure to high centrifugal forces.

This object is achieved according to the invention by a computed tomography apparatus having a drum mounted component, wherein the component is mounted on the drum such that a centrifugal force acting on it is the resulting force of a radially-proceeding vector and a substantially axially-proceeding vector, the substantially axially-proceeding vector being aligned on a support surface on the drum. Because the component is attached so that, given a rotation, the centrifugal force acting on it also has a substantially axial vector, the component is forced in the axial direction onto the support surface on the drum by this vector. The component is thus held more firmly on the drum as the centrifugal forces acting on it increase. As a consequence, possible fastening elements provided to secure the component are not stressed with increasing centrifugal force but instead are less stressed. In the operation of the tomography apparatus, an unwanted detachment of components can no longer occur.

In an embodiment, the support surface is on the drum base. It can be oriented transversally to the drum base in the direction of the drum cladding. Such a surface oriented transversely on the drum base can be produced with the drum base in a one-piece formation. It can also be mounted on the drum base, for example in the form of a shim fashioned as a support element.

The component itself also can exhibit a suitable sloped surface. In this case, the support surface on the gantry base is fashioned flat in the radial direction.

According to a further embodiment, a further support surface for support of the component is provided on an inner wall of the drum cladding. The further support surface preferably is oriented at an angle from the inner wall in the direction of the drum opening. The component can be supported on the further support surface such that it can move along rails in an essentially axial direction. This enables a movement of the components in the direction of the drum base. Such a movement can be caused by the centrifugal forces acting on the components. In a further embodiment, the movement is permitted only in the direction of the drum base, but not in the direction of the drum opening. For this purpose, for example, a projection jutting radially inwardly can be provided on the further support surface, the projection allowing a movement of the component only in the direction of the drum base.

According to a further embodiment, the component can have a first profile and a second profile corresponding to the first profile on a second support surface, such that the component can be connected on the second support surface by shifting the first profile into the second profile. The addressed profiles, for example, can be profiles formed as dovetails, grooves and corresponding tongues and the like. In a similar manner, profiles corresponding to one another can also be provided on the first support surface as well as on the components. They can also, for example, be groove and/or tongue profiles.

According to a further embodiment, the first profile and the second profile are fashioned such that the components are supported counter to the rotational direction of the drum. For example, for this purpose webs jutting radially inwards, between which the component is accommodated, can be provided on the further support surface. Given an acceleration and/or deceleration of the drum, such webs or similarly fashioned supports counteract the inertia of the component and support, and support these counter to the rotation direction of the drum.

A first centering element and a second centering element corresponding thereto are provided on the support surface, such that the component can be supported in a self-centering manner on the support surface upon exposure to centrifugal force. It is thereby ensured that the component always stays in an exact, appropriate mounting position. This is particularly important in x-ray computed tomography systems in which the exact position of the radiator and of the oppositely arranged detector has significant influence on the image quality.

The component can be fastened on the drum with at least one fastening element. This can be a screw, bolt or the like. According to the present invention, the fastening element essentially serves to secure the component, but not to absorb the forces on the drum that are caused by the centrifugal forces acting on the component. As a consequence, fastening elements that are dimensioned smaller or weaker (in comparison with conventional tomography apparatuses can be used.

DESCRIPTION OF THE PRIOR ART

FIG. 4 is a schematic axial section of a further embodiment of the profile shown in FIG. 2.

FIG. 5 is a sectional view taken along section line B–B' in FIG. 4.

FIG. 6 is a schematic axial section of a further embodiment of the profile shown in FIG. 2.

FIG. 7 is a partial radial section through a second embodiment of a gantry drum according to the invention.

FIG. 8 is a partial radial section through a third embodiment of a gantry drum according to the invention.

DESCRIPTION OF THE PREFERRED EMBODIMENTS

Figure 1:
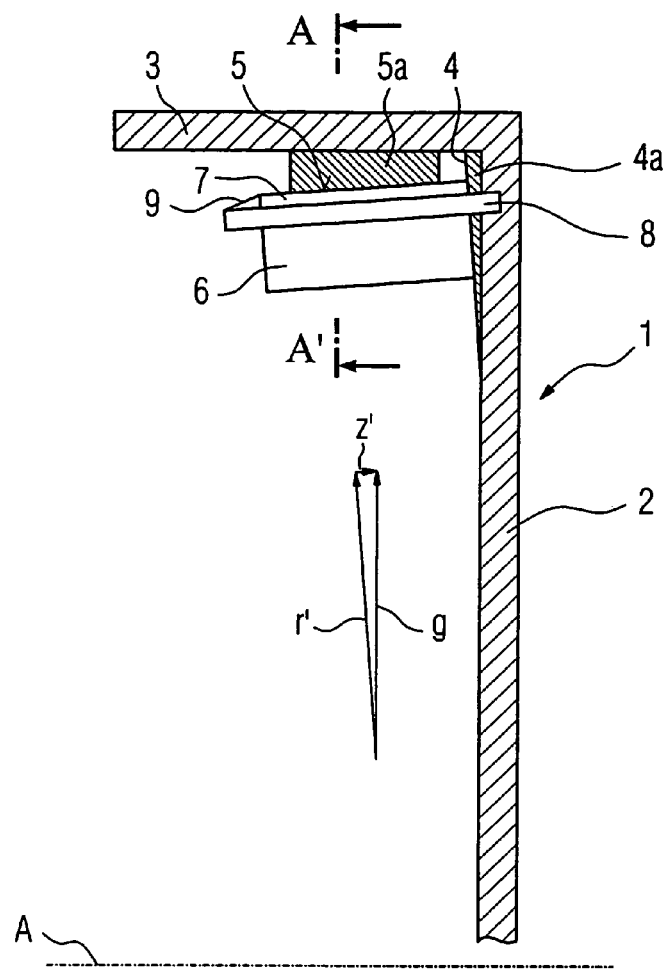
FIG. 1 is a partial radial section through a gantry drum in accordance with the invention, in a first embodiment.

FIG. 1 shows a partial radial section of a drum 1 of a tomography apparatus, the gantry 1 being rotatable around an axis A. The drum 1 is normally a rotatable part of a gantry of a known computer tomography apparatus (not shown here in detail). The drum 1 comprises a drum base 2 that, for example, is fashioned in the form of an annular ring. A circumferential drum shell 3 extends in the axial direction from a circumferential edge of the drum base 2. A first support surface 4 provided in the region of the circumferential edge of the drum base 2 is slanted with regard to the drum base 2 and projects radially inwardly. With the drum base 2, the first support surface 4 forms a first acute angle that opens toward the circumference edge of the drum base 2.

A second support surface 5 projecting radially inwardly is provided on an inner wall of the drum shell 3. The second support surface 5 is slanted relative to the inner wall of the generated surface 3. With the inner wall, it forms an acute angle that opens toward an opening of the drum 1. A component 6, for example an x-ray radiator, is supported at its housing on the first support surface 4 and the second support surface 5. The first support surface 4 can be a component of a first support element 4a which is mounted on the drum base 2. In the same manner, the second support surface 5 can be a component of a second support element 5a which can be mounted on the inner wall of the drum shell 3. The support surfaces 4, 5 can also be produced in a one-piece formation with the drum base 2 and/or the drum shell 3.

Figure 2:
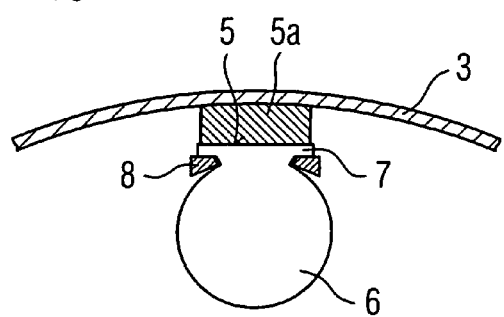
FIG. 2 is an axial section according taken along section line A–A' in FIG. 1.

As can be seen from FIG. 2, the component 6 is provided with a first profile 7 that interacts [cooperates] with a second profile 8 for fastening purposes. The second profile 8 is two rails extending from the drum base 2. For securing, the component 6 can be fastened in the region of the free ends of the rails, for example with fastening elements 9 in the form of a spring hinge.

Due to the slanted (with regard to a centrifugal force g acting on component 6 given a rotation of the drum 1) supports of the component 6 effected by the first support surface 4 and the second support surface 5, this centrifugal force g is decomposed into two components z.

The radial vector r', the axial vector z' and the resulting force g are shown in FIG. 1. As a result of the force exerted on the component 6 by the axial vector z', with increasing centrifugal forces this component 6 is forced against the first support surface 4 and against the second support surface 5. The fastening device acting in the form of the first profile 7 and in the form of the second profile 8 as well as the fastening elements 9 is unstressed given a rotation of the drum 1. The forces acting on the components 6 are absorbed by the first support surface 5 and the second support surface 5.

Figure 3:
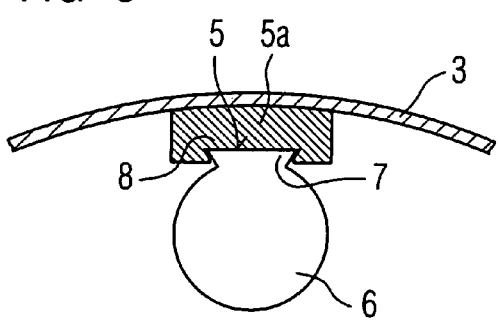
FIG. 3 is a schematic axial section of a further embodiment of the profile shown in FIG. 2.

In a schematic axial section, FIG. 3 shows a further embodiment of the first profile 7 and the second profile 8. In this case, the profiles are fashioned like dovetails. The second profile 8 is fashioned as one piece with the second support element 5a.

FIG. 4 through 6 show further embodiments of the first profile 7 as well as or the second profile 8. In these respective embodiments, a second support element 5a, which has the second support surface 5 thereon with the second profile 8 therein, is mounted on the inner wall of the drum shell 3. In the embodiment shown in FIGS. 4 and 5, the second profile 8 is formed by two webs 10 extending along the edge, the webs 10 supporting the component 6 counter to rotational movement of the drum 1. The embodiment shown in FIG. 6, in which the first profile 7 is fashioned in the form of an axially proceeding V-shaped rib, acts in a similar manner. In this case, the second profile 8 is fashioned correspondingly in the shape of a likewise axially extending V-shaped recess.

In the second embodiment of the drum 1 shown in FIG. 7, the component 6 exhibits a first profile 7 formed by a web extending in the circumferential direction of the drum 1. The second profile 8 is fashioned in the shape of a corresponding recess. In this exemplary embodiment, moreover, the component 6 is non-positively mounted on the drum base 2 by means of two fastening elements 11 (here in the form of screws).

In the drum 1 schematically shown in FIG. 8, a centering mandrel 12 extends from the drum base 2 and protrudes into a corresponding recess 13 in the component 6. The component 6e—as in the aforementioned exemplary embodiments—has a second support surface 5 that abuts a second support element 5a such that it can slide in the axial direction. Under the influence of centrifugal forces acting on the component 6, the component 6 is forced in the direction of the centering mandrel 12 as a result of the axial vector z. This embodiment thus is self-centering.

With the inventive apparatus, the component 6 can be securely held at a predetermined mounting location in the drum 1 of a tomography apparatus with extreme precision. Due to the supporting of the component 6 on the first slanted surface 4 and the second slanted surface 5, the disadvantageous effects of centrifugal forces as occur in the prior art, can be prevented. Breakage of fastening elements, and thus an unwanted detachment of the component 6 from the drum 1, thus can be prevented.

As noted above, the component 6 is fashioned with regard to the first support surface 4 and the second support surface 5 so that the support surfaces 4, 5 abut with a positive fit. This manner of mounting the component 6 on the drum 1 can be simply accomplished. For example, the component 6 merely has to be inserted, by means of the first profile 7 provided thereon, into the second profile 8 provided at the drum 1, and secured to the drum 1 by one or more fastening elements 9, 11, 14. In the self-centering embodiment, an extremely precise mounting of the component 6 on the drum 1 can be achieved in a simple and fast manner.

Although modifications and changes may be suggested by those skilled in the art, it is the intention of the inventor to embody within the patent warranted hereon all changes and modifications as reasonably and properly come within the scope of his contribution to the art.

I claim as my invention:

1. A tomography apparatus comprising:
    a gantry that is rotatable around a rotational axis, said gantry having a drum that is co-rotatable with said gantry, said rotational axis defining a radial direction relative thereto and an axial direction relative thereto;
    a component; and
    a mounting arrangement that mounts said component to said drum, said mounting arrangement comprising a support surface disposed on said drum and abutting said component and having a configuration that resolves a centrifugal force, acting on said component due to rotation of said drum, into a first force vector proceeding in said radial direction and a second force vector proceeding substantially in said axial direction, said second force vector being directed onto said support surface.

2. A tomography apparatus as claimed in claim 1 wherein said drum comprises a drum base, and wherein said support surface is disposed on said drum base.

3. A tomography apparatus as claimed in claim 1 wherein said drum comprises a drum shell connected substantially perpendicularly to said drum base, and wherein said supporting surface is slanted from said drum base in a direction of said drum shell.

4. A tomograph apparatus as claimed in claim 3 wherein said support surface is a first support surface and wherein said drum shell has an inner wall exposed to said first support surface, and wherein said mounting arrangement comprises a second support surface disposed on said inner wall of said drum shell.

5. A tomography apparatus as claimed in claim 4 wherein said drum has a drum opening, and wherein said second support surface is slanted from said inner wall in a direction toward said drum opening.

6. A tomography apparatus as claimed in claim 4 wherein said component comprises a first profile and wherein said second support surface comprises a second profiled complimentary to said first profile to hold said component in place in said mounting arrangement.

7. A tomography apparatus as claimed in claim 6 wherein said first profile and said second profile are configured to support said component counter to a rotational directional direction of said drum.

8. A tomography apparatus as claimed in claim 1 wherein said drum comprises a drum base, and wherein said mounting arrangement comprises a centering element projecting from said drum base and wherein said component comprises a centering recess complimentary to said centering element so that said component is self-centered in said mounting arrangement by engagement of said centering element with said centering recess.

9. A tomography apparatus as claimed in claim 1 wherein said mounting arrangement comprises at least one fastening element mechanically fastening said component to said drum.

10. A tomography apparatus as claimed in claim 1 wherein said drum comprises a drum base and a drum shell connected substantially perpendicularly to said drum base and having an inner wall exposed to said drum base, and wherein said support surface comprises a first support surface disposed on said drum base, and wherein said mounting arrangement comprises a second support surface, also abutting said component, disposed on said inner wall of said drum shell.

* * * * *